US005625036A

United States Patent [19]

Hawkins et al.

[11] Patent Number: 5,625,036
[45] Date of Patent: Apr. 29, 1997

[54] PREPARATION OF PROTHROMBIN TIME REAGENTS FROM RECOMBINANT HUMAN TISSUE FACTOR AND PURIFIED NATURAL AND SYNTHETIC PHOSPHOLIPIDS

[75] Inventors: Pamela L. Hawkins, Hialeah; Liliana Tejidor, Miami; James Maynard, Miami; Kevin B. Johnson, Miami, all of Fla.

[73] Assignee: Dade International Inc., Deerfield, Ill.

[21] Appl. No.: 371,052

[22] Filed: Jan. 10, 1995

Related U.S. Application Data

[63] Continuation of Ser. No. 32,562, Mar. 17, 1993, abandoned, which is a continuation of Ser. No. 771,294, Oct. 4, 1991, abandoned.

[51] Int. Cl.$^6$ .............................. C07K 4/00; C12Q 1/56
[52] U.S. Cl. ........................... 530/381; 530/350; 435/13
[58] Field of Search .............................. 530/350, 381; 435/13

[56] References Cited

U.S. PATENT DOCUMENTS

| | | | |
|---|---|---|---|
| 4,461,833 | 7/1984 | Gordon | 435/183 |
| 4,721,572 | 1/1988 | Jordan | 210/635 |
| 4,865,984 | 9/1989 | Nemerson et al. | 435/287.1 |
| 5,439,802 | 8/1995 | Rosén | 435/13 |

FOREIGN PATENT DOCUMENTS

| | | |
|---|---|---|
| 0014039 | 8/1980 | European Pat. Off. . |
| WO890084 | 6/1987 | WIPO . |
| WO9208479 | 5/1992 | WIPO . |
| 9218870 | 10/1992 | WIPO . |

OTHER PUBLICATIONS

Prothrombin Time Reagents Prepared from Recombinant Human Tissue Factor Produced in *E coli*. P. Hawkins et al. Thrombosis and Haemostasis (1991) 645–1417 vol. 65(6).
Biochemistry 25 (14) 1986; 4007–4020. Bach, R. "Factor VII binding to tissue factor in reconstituted phospholipid vesicles: Induction of cooperativity by phosphatitidylserine."
Dade$^R$ Thromboplastin IS, Dried Rabbit Brain Thromboplastin with Calcium. Baxter Healthcare Corp. 1989.
Dade$^R$ Thromboplastin C Plus, Dried Rabbit Brain Thromboplastin with Calcium. Baxter Healthcare Corp. 1990.
Dade$^R$ Thromboplastin C, Dried Rabbit Brain Thromboplastin with Calcium. Baxter Healthcare Corp. 1989.

Nemerson, Y. "Tissue Factor and Hemostasis", Blood: 71 1, 1–8 (1988).
Paborsky, Lisa R. et al., "Purification of Recombinant Tissue Factor", Biochemistry; 28 20, 8072–8077 (1989).
Spicer, Eleanor K. et al., "Isolation of cDNA cones coding for human tissue factor: Primary structure of the protein and cDNA", Proceedings of the National Academy of Science; 84, 5148–5152 (1987).
Bach, Ronald, "Initiation of Coagulation by Tissue Factor", CRC Critical Reviews in Biochemistry; 23 4, 339–368 (1988).
Bach, Ronald et al., "Pruffication and Characterization of Bovine Tissue Factor", Journal of Biol. Chem.; vol. 256 16, 8324–8331 (1981).
Brown, Scott M. et al., "Development of a human Recombinant Tissue Factor Prothrombin Time Reagent", Clin. Chem.; 37 6, 951 (1991).
Chargaff, Erwin, et al., "The Thromboplastic Protein: Structure Properties, Disintegration", J. biol. Chem; 156, 161–178 (1944).
Fisher, Karen et al., "Cloning and Expression of Human Tissue Factor cDNA", Thrombosis Research; 48, 89–99 (1987).
Lawson, Jeffrey H. & Mann, Kenneth G. "Cooperative Activation of Human Factor IX by the Human Extrinsic Pathway of Blood Coagulation" J. Biol. Chem; 266 17, 11317–11327 (1991).
Roy et al. Journal of Biochemistry, 266:4665–4668. 1991.
Scarpati et al. Biochemistry, 26:5234–5238. 1984.
Liang et al. Biochemical and Biophysical Research Communications, 137:847–854. 1986.
Ruf et al. Journal of Biological Chemistry, 266:2158–2166. 1991.
Wang et al. Biochemical Journal, 276:63–71. 1991.
Rehemtulla et al. Thrombosis and Haemostasis, 65:521–527. 1991.

*Primary Examiner*—George C. Elliott
*Assistant Examiner*—Thanda Wai
*Attorney, Agent, or Firm*—Cynthia Tymeson

[57] ABSTRACT

A prothrombin time reagent is disclosed for use in a prothrombin time test. The reagent utilizes recombinant human tissue factor, phospholipids of a natural or synthetic origin, a buffer composition and calcium ion. Stabilizers and salts may also be utilized in the reagent. In addition, a method for creating lipid micelles containing tissue factor is also disclosed.

11 Claims, 2 Drawing Sheets

PREPARATION OF PROTHROMBIN TIME REAGENTS FROM RECOMBINANT HUMAN TISSUE FACTOR AND PURIFIED NATURAL AND SYNTHETIC PHOSPHOLIPIDS

This is a continuation of application Ser. No. 08/032,562, filed on 3/17/93, abandoned, which is a continuation of application Ser. No. 07/771,294, filed on 10/4/91, abandoned.

FIELD OF THE INVENTION

The present invention relates generally to the field of Prothrombin Time reagents for determining dysfunction in the coagulation system and more specifically to reagents made from recombinant human tissue factor and phospholipids from a natural or synthetic source for Prothrombin Time tests. The present invention also includes a method to combine tissue factor with phospholipids.

DESCRIPTION OF THE PRIOR ART

Tissue factor, also called thromboplastin, is a membrane-associated glycoprotein which functions by forming a complex with blood coagulation factors VII and VIIa. The complexing of these factors greatly enhances the proteolytic activity of factors VII and VIIa. Functional activity of tissue factor has an absolute dependence on the presence of phospholipids. Bach, Ronald R., *Initiation of Coagulation by Tissue Factor*, CRC Critical Reviews in Biochemistry 1988; 23 (4): pp. 339–368. The factor VII/VIIa/tissue factor complex activates a series of specific enzymes that comprise the extrinsic and common pathways of the coagulation cascades ultimately leading to the formation of thrombin, fibrin, platelet activation, and finally clot formation. Nemerson, Yale, *Tissue Factor and Hemostasis*, Blood 1988; 71: pp. 1–8.

Diagnostic tests such as the Prothrombin Time (PT) test, utilize this series of enzymatic events in vitro under controlled conditions to diagnose dysfunctions in the blood coagulation system of patients. In the PT test, the time it takes for clot formation to occur is the Prothrombin Time or PT value.

All currently available PT tests utilize a PT reagent containing crude tissue factor extracted from natural sources. It is important for a PT reagent to have the following characteristics: sensitive to abnormal samples, a well defined normal PT value for normal plasma, give accurate and reproducible results, have lot-to-lot consistency, must be stable for storage in the freeze-dried (lyophilized) state and must be stable after reconstitution.

Currently, the tissue factor used in the PT reagents is a crude tissue factor preparation extracted from rabbit brain, rabbit brain/lung mixtures, human placenta or ox brain. Each of these sources has limitations that make them problematic. For example, rabbit brain thromboplastin shows some seasonal variability, lot-to-lot variability and is in relatively short supply. Human tissue factor may be a source of HIV or other human viral diseases, and ox brain gives normal PT values that are much longer than those observed using tissue factor from the other common sources. Longer PT values lead to less throughput in the laboratory. Additionally, these longer times may reflect differences in the ability of ox tissue factor to bind human factor VII. Moreover, crude tissue factor preparations from natural sources contain other coagulation factors as contaminants. Contamination with coagulation factors results in coagulation factor assay curves that are less sensitive to coagulation factor-deficient plasmas. Therefore, a source of tissue factor which does not suffer from these drawbacks and has improved lot-to-lot variability is required to create a more reproducible PT reagent. Recently, use of recombinant tissue factor has been suggested for use in the currently available PT tests. Pabrosky, L. et al, *Purification of Recombinant Human Tissue Factor*, Biochemistry 1989; 28 (20): pp. 8072–8077.

In the present invention, human tissue factor, which has just recently been cloned and expressed in several types of organisms including *E. coli*, is used in the PT reagent to solve these problems. Konigsberg W. H., Nemerson, Y. et al. *Isolation of cDNA clones coding for human tissue factor: Primary structure of the protein and cDNA*, Proc. Natl. Acad. Sci. 1987; 84: pp. 5148–5152. In addition, the present invention can use a portion of the cloned tissue factor in the PT reagent. For example most of the intracellular (cytoplasmic) domain of the cloned tissue factor can be truncated without loss of functional activity. Further, point mutations, such as the conversion of Cys 245 to serine can be accomplished without loss of functional activity. Pabrosky L., et al, *Purification of Recombinant Human Tissue Factor*, Biochemistry 1989: 28 (20) pp. 8072–8077.

As previously mentioned, tissue factor has an absolute requirement for phospholipids for functional activity. The phospholipids currently found in PT reagents are however, those lipids that adhere to tissue factor when it is extracted from animal sources. For example, the extraction process of rabbit brain results in the concurrent isolation of both tissue factor and naturally occurring phospholipids which are bound to the tissue factor in vivo and survive the extraction process. No further lipids are added. Therefore the nature, quantity and quality of the lipids used in the PT reagent will vary depending on the starting tissues and the extraction process. This variation may add to lot-to-lot inconsistencies in PT reagents. The Dade® thromboplastin reagents, Thromboplastin C, C+, and IS, are all based on extracts of acetone-dehydrated rabbit brain. The partially purified extracts are blended with specific mixtures of buffers and stabilizers. The partially purified tissue factor extract is not completely delipidized therefore lipids are not added back into the extract, and the nature and composition of the lipids are poorly defined and variable from lot-to-lot.

In vitro tissue factor studies have shown phosphatidyl serine: phosphatidyl choline in the range of 20:80 to 40:60 restore the activity of apo-tissue factor. Nemerson, Yale, *Tissue Factor and Hemostasis*, Blood 1988; 71: pp. 1–8. The nature of the polar head group on the phospholipid dramatically alters the activity of tissue factor. Bach, Ronald, *Initiation of Coagulation by Tissue Factor*, CRC Critical Reviews in Biochemistry 1988; 23 (4): pp. 339–368. Generally, however, the phospholipids used in PT reagents have not been well characterized. A well defined and reproducible composition of phospholipids is needed to provide an improved PT reagent.

SUMMARY OF THE INVENTION

This invention relates to PT reagents prepared using purified recombinant human tissue factor (rTF). This invention also describes the use of highly purified well defined lipids, either synthetic or natural in combination with the recombinant or native tissue factor. By controlling the tissue factor source and purity and using highly purified lipids in conjunction with well defined specific buffers and stabilizers, control of the performance of tissue factor in a PT reagent is improved.

The present invention is a PT reagent that comprises the following: recombinant tissue factor, phospholipids, either synthetic or natural, calcium ion, and a buffer composition and may also have stabilizers such as glycine or dextrans, and salts such as NaCl.

The preferred embodiment of the present invention uses a recombinant tissue factor or portion thereof obtained by the methods of Nemerson or Pabrosky. Konigsberg W. H., Nemerson, Y. et al. *Isolation of cDNA clones coding for human tissue factor: Primary structure of the protein and cDNA*, Proc. Natl. Acad. Sci. 1987; 84: pp. 5148–5152. Pabrosky L., et al. *Purification of Recombinant Human Tissue Factor*, Biochemistry 1989: 28 (20) pp. 8072–8077. The preferred embodiment of the invention comprises rTF, which may be truncated or contain point mutations which have comparable activity, at a concentration of about 20 to 400 ng/mL, a phospholipid composition containing, preferably, either purified natural or synthetic phosphatidyl serine:phosphatidyl choline and synthetic derivatives thereof in the ratios of about 30:70 and having a tissue factor:phospholipid molar ratio of about 1:2000 to 1:20,000, and buffers and stabilizers. The buffers of the preferred embodiment are selected from the group consisting of HEPES, TAPSO, MOPS, TES, DIPSO, POPSO, and TRIS in a concentration of about 20 to 80 mM, however other buffers may be used. The bulking agents of the preferred embodiment include glycine in the range of about 0–10% and dextran from about 0–5%, however other agents may be used. The preferred embodiments also contain from about 9 to 15 mM calcium ion and may include about 0 to 300 mM NaCl.

The present invention also comprises a method to combine tissue factor with phospholipids. The phospholipids are solubilized in a detergent with a critical micelle concentration high enough to allow its dialysis or diafiltration. The tissue factor is also dissolved in a detergent and combined with the phospholipids. The mixture then undergoes dialfiltration in a tangential flow system, making contact with the exterior of the membrane. The diafiltration is continued until essentially all the detergent is removed.

In accordance with this invention, a PT reagent is provided which has a high degree of sensitivity and reproducibility for determining PT values. A further object of this invention is to provide a PT reagent which is sensitive to the overall function of the coagulation system. Another object of this invention is to provide a PT reagent with a well-defined clotting time for normal plasma samples and which prolongs the clotting times of abnormal plasma samples. It is a further object of this invention to provide a PT reagent with minimal lot-to-lot variability and enhanced stability and optical clarity. It is a further object of this invention to provide a method to combine the rTF with the phospholipids which is more efficient and reproducible than current methods.

The advantages and composition of the present invention will be better understood by reference to the following detailed description and Examples.

DETAILED DESCRIPTION OF THE PREFERRED EMBODIMENT

Figure 1:
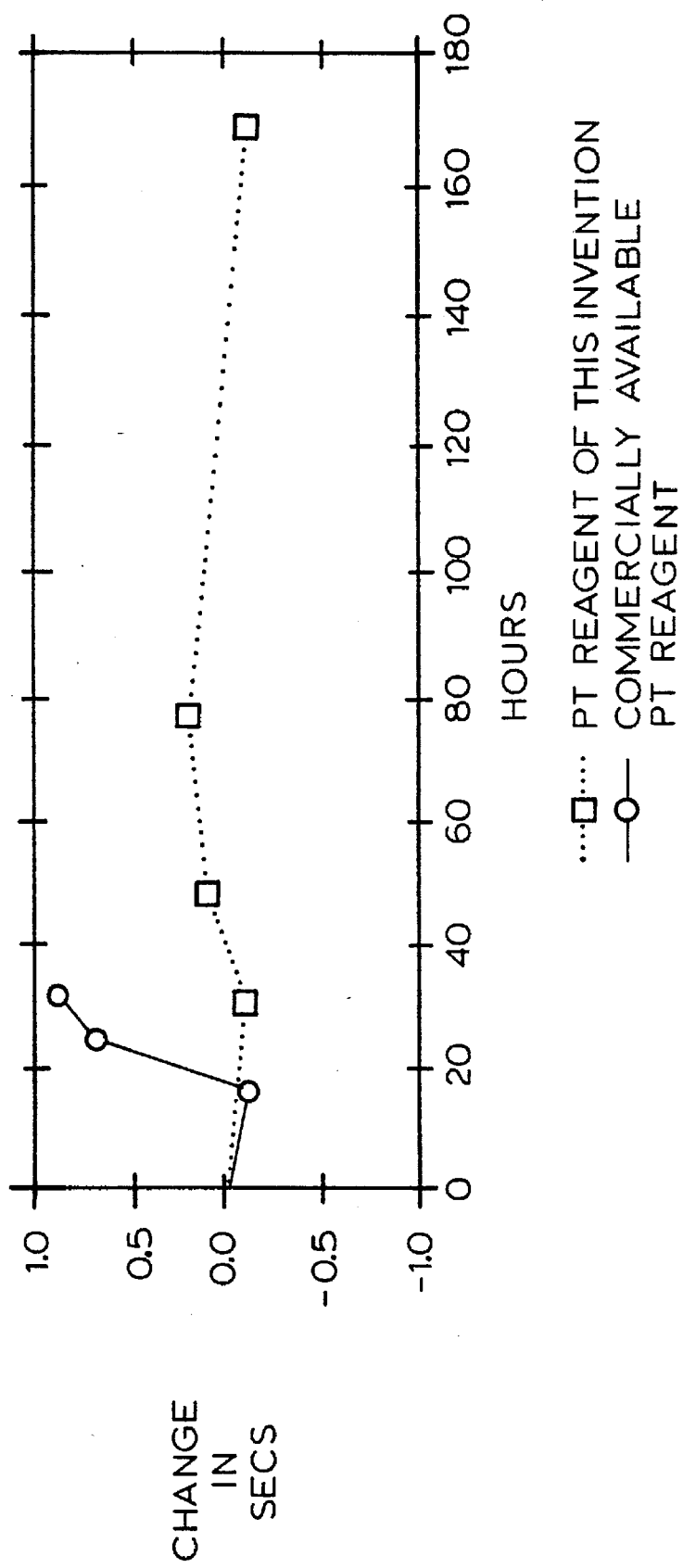
FIG. 1 is a graph showing the improvement in stability of a reconstituted lyophilized PT reagent of this invention over a commercially available reagent.

The advantage that the preferred embodiment of the present invention has over the prior art is that it uses a well defined, purified rTF protein in combination with purified, well defined phospholipids. Full length as well as truncated recombinant molecules can be used pursuant to the methods of Nemerson and Pabrosky. The present invention also encompasses a rTF with additions, deletions and substitutions of amino acids that do not diminish the functional activity of the PT reagent. The preferred modification of rTF is truncated at or about amino acid residue 243. The preferred concentrations of rTF in the PT reagent are from about 20 to 400 ng/mL and most preferably about 40 to 250 ng/mL. PT reagents made from these raw materials are optically clear without the fine precipitates found in PT reagents based on crude extracts of natural source materials. Since the raw materials are highly purified, chemical analysis gives a meaningful measure of their expected performance. Chemical analysis, in combination with functional assays, help provide lot-to-lot consistency, an important clinical consideration. Table I shows a comparison of three different lots of a PT reagent made using rTF. Results demonstrate the consistency of the lots by comparing PT values from a normal plasma, a normal control, an abnormal control and a warfarinized sample.

TABLE I

| | Lot to Lot Reproducibility | | | |
|---|---|---|---|---|
| Lot No. | Normal Plasma | Warfarin Plasma | Normal Control | Abnormal Control |
| 1 | 11.5 | 33.9 | 11.3 | 28.1 |
| 2 | 11.8 | 32.4 | 11.4 | 25.9 |
| 3 | 12.0 | 30.4 | 11.2 | 30.4 |

Naturally occurring phospholipids used in the PT reagent containing recombinant TF include natural phosphatidyl serine (PS) in the range from about 25 to 35% of total phospholipid with the most preferred at about 30% and natural phosphatidyl choline (PC) in the range from about 65 to 75% of total phospholipid with the most preferred at about 70%. The phosphatidyl choline used is neutral in charge, while the phosphatidyl serine is negatively charged. In the preferred embodiment the lipids have an overall negative charge. In other embodiments of this invention it is possible to use combinations of other lipids. A tissue factor:phospholipid molar ratio of about 1:2,000 to 1:20,000 is required with the most preferred ratio being about 1:10,000. This results in a PT reagent with a total phospholipid concentration of about 1–300 μM. A preferred source of the natural PS is from bovine brain and a preferred source of the natural PC is from egg yolk.

Synthetic phospholipids may also be used with the present invention. These synthetic compounds may be varied and may have variations in their fatty acid side chains not found in naturally occurring phospholipids. The side chain variations that result in PT reagent improvement are unsaturated fatty acid side chains with C14, C16, or C18 chains length in either or both the PS or PC. Preferred compositions include but are not limited to those that have dioleoyl (18:1)-PS, palmitoyl (16:0)-oleoyl (18:1)-PS, dimyristoyl (14:0)-PS, dipalmitoleoyl (16:1)-PC, dipalmitoyl (16:0)-PC, dioleoyl (18:1)-PC, palmitoyl (16:0)-oleoyl (18:1)-PC, and myristoyl (14:0)-oleoyl (18:1)-PC as constituents.

Optimal activity of the PT reagent is achieved when the tissue factor:synthetic phospholipid ratios are about 1:2,000 to 1:20,000 with the preferred ratio being about 1:10,000. This leads to a final concentration of about 1–300 μM of total phospholipids. Thus both the PS:PC and rTF to total phospholipid ratio are essential to achieve and maintain optimal functional activity.

The PT reagents made from recombinant or natural purified tissue factor in combination with natural phospholipids and synthetic phospholipids with and without variation in side chains offers an improvement in the quality and sensitivity of the PT reagent. Synthetic phospholipids give the advantage of a more reproducible final product and offer the improvement of better controlled functional activity of the PT reagent when the side chains are varied.

The choice of buffers and stabilizers vary widely and can also assist in the stability of the PT reagent. The most preferred embodiments may include calcium ion in the concentration range from about 9 to 15 mM, NaCl in the concentration range from about 0 to 300 mM, bulking agents such as glycine in the concentration range from about 0 to 10% with the most preferred range from about 2 to 5%, dextran in the range of about 0 to 5%, and an appropriate buffer. Buffer, such as N-2-Hydroxyethylpiperazine-N'-2-aminoethane sulfonic acid (HEPES), 3-[N-(Tris-hydroxymethyl) methylamino]-2-hydroxy-propane sulfonic acid (TAPSO), 3-(N-Morpholino) propane sulfonic acid (MOPS), N-Tris-(hydroxymethyl) methyl-2-aminoethane sulfonic acid (TES), 3-[N-bis(hydroxyethyl)-amino] 2-hydroxypropane sulfonic acid (DIPSO), Piperazine-N, N'bis (2-hydroxypropane-sulfonic acid) (POPSO), N-Hydroxyethylpiperazine-N'-2-hydroxypropane sulfonic (HEPPSO) and Tris-(hydroxymethyl) aminomethane (TRIS) are preferred in the PT reagent. The most preferred buffers are HEPES or TAPSO in the concentration range of about 20 to 80 mM.

In the preferred embodiment of this invention, the raw material recombinant human tissue factor is grown in vitro in *E. coli*, extracted with a detergent solution and then purified using affinity chromatography methods on immobilized monoclonal antibodies directed against human tissue factor. Bach, Ronald R., *Initiation of Coagulation by Tissue Factor*, CRC Critical Reviews in Biochemistry 1988; 23 (4): pp. 339–368.

In the method of this invention, the purified tissue factor is combined with mixtures of either purified natural or specific synthetic phospholipids as previously described. This process is performed by mixing the recombinant protein in a detergent, such as octylglucoside or a similar detergent, with the phospholipids, also solubilized in a detergent solution. The detergents should have a critical micelle concentration high enough to allow diafiltration. The detergents are then removed by a diafiltration or dialysis process to form lipid micelles that contain the tissue factor.

The diafiltration is accomplished as follows: Phospholipids of this invention for example, phosphatidyl choline: phosphatidyl serine at about a ratio of about 70:30, either natural or synthetic are solubilized by vortexing, mixing, heating and/or water bath sonication in a detergent with a critical micelle concentration high enough to allow its diafiltration. The phospholipids of the mixture are at about 8 to 20 mM and preferably at 10 mM. The critical micell concentration of the detergent preferably is greater than about $1 \times 10^{-4}$ m/L with the most preferred concentration at about $2.5 \times 10^{-2}$ m/L. For example, with octylglucoside or other similar detergents, the lipids preferably can be solubilized in a concentration range of detergent at about 11 mg/mL to 220 mg/mL, and most preferably at about 110 mg/mL. The lipid mixtures are combined at room temperature with rTF dissolved in a range from about 0.1 to 10% detergents and preferably at about 1% octylglucoside or other detergents. The other detergents of this invention may include non-ionic glucopuranosides, polyoxyethylene and non-denaturing zwitterionic detergents. The preferred detergent is octylglucoside. The lipid/rTF mixtures are immediately diluted about 1:1 with buffer and pumped in the vessel of a Membrex Benchmark® GX Biofiltration System, or other tangential flow system, making contact with the exterior of the membrane. As detergent flows out through the pores of the membrane, buffer is pumped in. The sample is being re-circulated during this process and the biofiltration membrane is rotating to prevent lipid build-up at the surface and to force buffer through the filter. Alternatively, lipid build-up may be prevented by sweeping material tangential to the filter surface such as occurs with any tangential flow filtration device. Alternatively, the membrane is stationary as in the Membrex Pacesetter® VFF System. Vortices that sweep the membrane are generated by the movement of a rotor that runs down the center of the membrane. Alternatively, if the detergents used to dissolve the rTF and the phospholipids are the same detergent at the same concentration, then the rTF and the phospholipids may be added together.

After about 20–50 volumes of buffer, the detergent removal is complete and lipid micelles containing rTF have been formed. To ensure that detergent removal is complete, a PT assay is performed using normal and abnormal control plasmas. A prolongation in PT times and high ratios of abnormal to normal PT values indicate that residual detergent is still present. The sample is concentrated and assayed for functional activity. The diafiltration process is more efficient and reproducible than current processes which use dialysis. The diafiltration process requires much less volume and is less time consuming than the current dialysis processes that are employed. The detergent-free protein:phospholipid mixture is then added to a solution of buffers and stabilizers. The mixture is stirred to ensure homogeneity, dispensed into vials and then frozen and freeze-dried (lyophilized). The dried reagent is reconstituted to its active form by the addition of water.

PT values can be determined by any of the commonly used end point detection methods including mechanical and photo-optical instruments. The enhanced clarity of PT reagents based on this composition is particularly advantageous for photo-optical instruments.

The PT reagents of this invention show an improved stability before and after reconstitution over commercially available PT reagents. Table II shows the improvement in stability of PT values using a normal control tested with a reconstituted truncated rTF PT reagent compared with a commercially available reagent.

TABLE II

| | Comparison of Reconstituted Stability | |
|---|---|---|
| Temperature | PT Reagent of This Invention | PT Reagent Available Commercially |
| 37 C. | 24 hours | 8 hours |
| 25 C. | 5 days | 1 day |
| 2–8 C. | 10 days | 5 days |

FIG. 1 demonstrates this stability graphically. A lyophilized PT reagent of this invention which was prepared with a truncated rTF and a commercially available PT reagent were reconstituted and stored at 37 C. At various hours, a normal control was tested with both types of PT reagents. The PT values obtained were compared with PT values obtained for the same normal control using freshly reconstituted PT reagents of both types. The PT reagent of this invention shows an improved reconstituted stability over the commercially available PT reagent.

Figure 2:
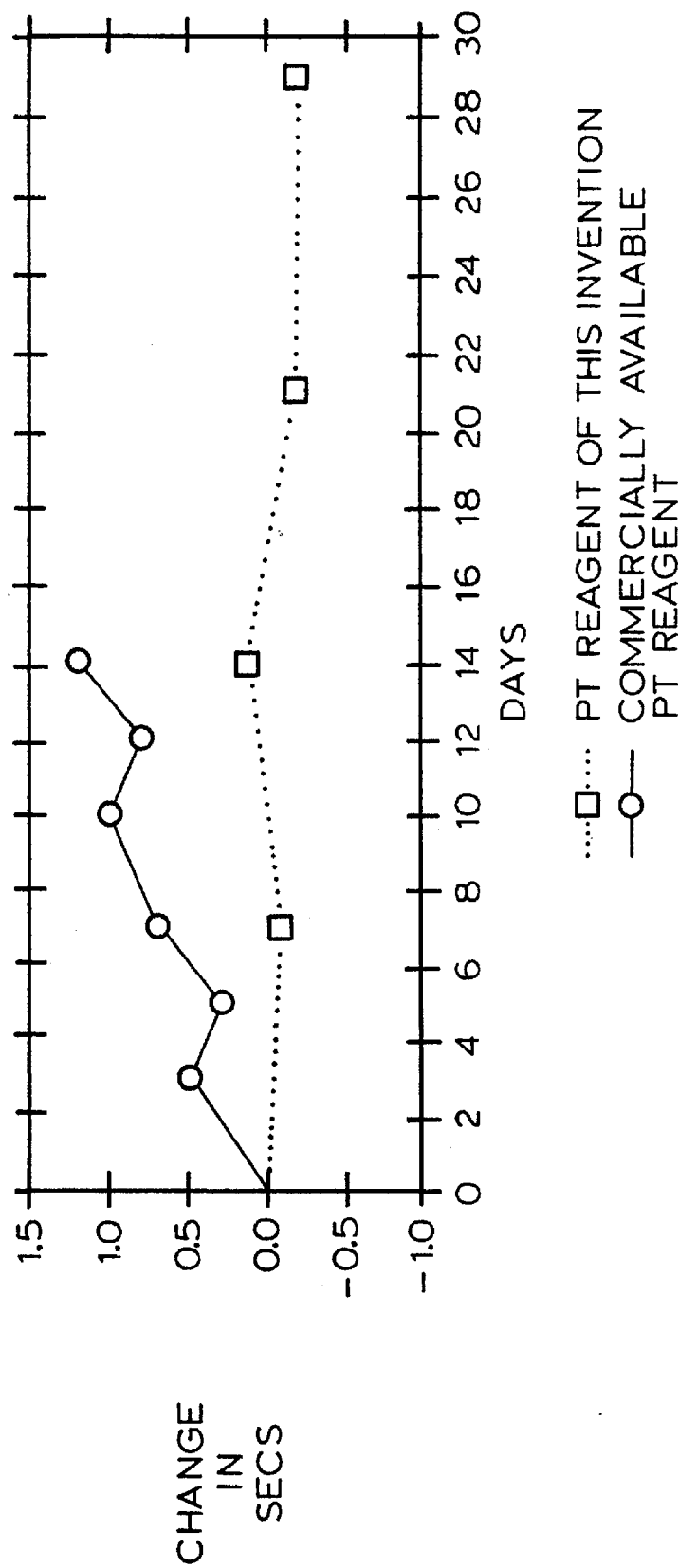
FIG. 2 is a graph showing the improvement in stability of a lyophilized PT reagent of this invention over a commercially available reagent.

FIG. 2 demonstrates the improvement in unreconstituted (dried) stability at 37 C. of a truncated rTF lyophilized PT reagent when compared with a commercially available reagent. The data was obtained by storing several unreconstituted vials of each type of PT reagent at 37 C. and reconstituting a fresh vial of both types of PT reagents on the indicated days. Vials stored at 2–8 C. for both types of PT reagents were used as a control for both types of PT reagent. The normal control was tested on these days and PT values obtained using the vials stored at 37 C. were compared to the PT values obtained for vials stored at 2–8 C. at each day for both types of PT reagents. The difference in PT values between vials stored at the two temperatures was calculated and the change was plotted against the days tested. The PT reagent of this invention shows an improved unreconstituted stability over the commercially available PT reagent.

EXAMPLE 1

PT Reagents made using Full Length recombinant Human Tissue Factor and Natural Phospholipids— Effect of Varying rTF Concentration Various concentrations of recombinant human tissue factor were lipidated with purified bovine phosphatidyl serine (PS) and purified egg phosphatidyl choline (PC) in a PS:PC ratio of 30:70 and a molar ratio of 1:10,000 rTF:phospholipid. The formulation also included 50 mM TAPSO, 11 mM CaCl$_2$, 2.6% glycine, 2.6% dextran, pH 7.4. Results are given as clotting times and were determined using an MLA Electra 800 photo-optical coagulation timer. Two commercial PT reagents based on rabbit brain tissue factor, Thromboplastin C+ and Thromboplastin IS, are included for comparison. The test plasmas are a normal lyophilized control, Ci-Trol 1 (COL 1), an abnormal lyophilized control, Ci-Trol II (COL 2), a pool of fresh normal plasma (FNP), and a lyophilized pool of plasmas from patients receiving warfarin (WARFARIN). The column under WAR/FNP is the ratio of the PT value of the warfarinized plasma pool divided by the PT value of the normal plasma pool. This ratio is a measure of sensitivity of the reagents. See Data Table I.

DATA TABLE 1

| rTF Concentration (ng/mL) | COL 1 | COL 2 | FNP | WARFARIN | WAR/FNP |
|---|---|---|---|---|---|
| 12.5 | 12.7 | 28.4 | 13.1 | 31.6 | 2.41 |
| 25.0 | 11.5 | 26.2 | 11.8 | 28.1 | 2.31 |
| 50.0 | 10.5 | 24.2 | 10.6 | 25.8 | 2.43 |
| 100.0 | 9.5 | 23.0 | 9.6 | 24.5 | 2.55 |
| 150.0 | 9.1 | 23.1 | 9.2 | 24.5 | 2.66 |
| 200.0 | 8.9 | 23.1 | 9.0 | 24.8 | 2.76 |
| 300.0 | 8.9 | 23.8 | 8.8 | 25.4 | 2.89 |
| 400.0 | 8.9 | 24.4 | 8.7 | 26.4 | 3.03 |
| THROMBOPLASTIN C+ | 11.8 | 22.9 | 11.7 | 24.4 | 2.09 |
| THROMBOPLASTIN IS | 14.3 | 35.4 | 13.4 | 37.1 | 2.77 |

EXAMPLE 2

PT Reagents made using Full Length recombinant Human Tissue Factor and Natural Phospholipids— Effect of Varying rTF:Phospholipid Ratio (Lyophilized Reagents)

Recombinant human tissue factor, at either 145 ng/mL or 200 ng/mL, was combined with a mixture of purified bovine phosphatidyl serine (PS) and purified egg phosphatidyl choline (PC) in a PS:PC ratio of 30:70. In the example shown, two molar ratios of rTF:phospholipid, 1:10,000 and 1:20,000 rTF:phospholipid, were used. The first formulation (10S, 20S) with 145 ng/mL rTF, also included 68 mM TAPSO, 11 mM CaCl$_2$, 140 mM NaCl, 5.2% glycine, pH 7.4. The second formulation (10F, 20F) with 200 ng/mL rTF, also included 50 mM TAPSO, 11 MM CaCl$_2$, 140 mM NaCl, 5.2% glycine, pH 7.4. The formulations were dispensed into vials and freeze-dried. Results are given as clotting times and were determined using an MLA Electra 700 photo-optical coagulation timer. A commercial PT reagent, Thromboplastin IS, is included for comparison. The test plasmas are a normal lyophilized control, Ci-Trol 1 (COL 1), an abnormal lyophilized control, Ci-Trol II (COL 2), a pool of fresh normal plasma (FNP), and a lyophilized pool of plasmas from patients receiving warfarin (WARFARIN). The column under WAR/FNP is the ratio of the PT value of the warfarinized plasma pool divided by the PT value of the normal plasma pool. This ratio is a measure of sensitivity of the reagents. See Data Table 2.

DATA TABLE 2

| FORMULATION rTF:LIPID | COL 1 | COL 2 | FNP | WARFARIN | WAR/FNP |
|---|---|---|---|---|---|
| 10S (1:10,000) | 11.0 | 28.5 | 9.9 | 37.1 | 3.75 |
| 20S (1:20,000) | 11.8 | 30.8 | 10.6 | 40.1 | 3.78 |
| 10F (1:10,000) | 11.0 | 28.7 | 9.9 | 39.2 | 3.96 |
| 20F (1:20,000) | 12.1 | 31.9 | 10.8 | 44.5 | 4.12 |
| THROMBOPLASTIN IS | 15.0 | 40.9 | 14.0 | 45.3 | 3.24 |

EXAMPLE 3

PT Reagents made using Full Length recombinant Human Tissue Factor and Synthetic Phospholipids—Effect of Varying the Nature of the Fatty Acid Side Chain Moiety of the Phospholipid Purified recombinant human tissue factor, at either 100 or 300 ng/mL, was combined with mixtures of synthetic phosphatidyl serine (PS) and synthetic phosphatidyl choline (PC) in a PS:PC ratio or 30:70 and a ratio of rTF:phospholipid of 1:10,000. The formulation also included 50 mM TAPSO, 11 mM CaCl$_2$, 100 mM NaCl, pH 7.4. Results are given as clotting times and were determined using an MLA Electra 800 photo-optical coagulation timer. Recombinant tissue factor lipidated with natural phospholipids, bovine PS and egg PC, was used as a control. The test plasmas are a normal lyophilized control, Ci-Trol 1 (COL 1), an abnormal lyophilized control, Ci-Trol II (COL 2), and a lyophilized pool of plasmas from patients receiving warfarin (WARFARIN). The column under RAT is the ratio of the ratio of the PT value of the warfarinized plasma pool divided by the PT value of COL 1. This ratio is a measure of sensitivity of the reagents. See Data Table 3.

DATA TABLE 3

| PS Description | PC Description | RTF ng/mL | COL 1 | COL 2 | WARF | RAT. |
|---|---|---|---|---|---|---|
| Dimyristoyl (14:0) | Dilauroyl (12:0) | 100 | 24.3 | 54.2 | 53.1 | 2.19 |
|  |  | 300 | 19.1 | 46.6 | 44.6 | 2.34 |
| Dimyristoyl (14:0) | Dimyristoyl (14:0) | 100 | 40.4 | >100 | 82.7 | 2:05 |
|  |  | 300 | 41.1 | >100 | 100 | 2.43 |
| Dimyristoyl (14:0) | Dipalmitoyl (16:0) | 100 | 96.3 | >100 | >200 |  |
|  |  | 300 | 93.2 | >100 | >200 |  |
| Dimyristoyl (14:0) | Dipalmitoleoyl (16:1) | 100 | 16.9 | 38.4 | 35.8 | 2.12 |
|  |  | 300 | 14.1 | 33.5 | 29.7 | 2.11 |
| Palm (16:0)-oleoyl (18:1) | Dimyrstoyl (14:0) | 100 | 17.7 | 38.3 | 34.7 | 1.96 |
|  |  | 300 | 16.4 | 37.8 | 35.6 | 2.17 |
| Dioleoyl (18:1) | Dipalmitoleoyl (16:1) | 100 | 10.2 | 23.1 | 19.3 | 1.89 |
|  |  | 300 | 10.0 | 22.6 | 19.2 | 1.92 |
| Palm (16:0)-oleoyl (18:1) | Dipalmitoleoyl | 100 | 11.8 | 24.5 | 21.1 | 1.79 |
|  |  | 300 | 10.2 | 24.1 | 19.4 | 1.90 |
| Dimyristoyl (14:0) | Dioleoyl (18:1) | 100 | 11.2 | 26.5 | 22.7 | 2.03 |
|  |  | 300 | 10.4 | 26.7 | 22.4 | 2.15 |
| Palm (16:0)-oleoyl (18:1) | Dioleoyl (18:1) | 100 | 10.3 | 24.4 | 19.2 | 1.86 |
|  |  | 300 | 9.5 | 25.4 | 20.0 | 2.11 |
| Dioleoyl (18:1) | Dipalmitoyl (16:0) | 100 | 12.8 | 29.5 | 23.8 | 1.86 |
|  |  | 300 | 11.0 | 27.8 | 21.8 | 1.98 |
| Palm (16:0)-oleoyl (18:1) | Dioleoyl (18:1) | 100 | 11.3 | 26.9 | 20.6 | 1.82 |
|  |  | 300 | 9.9 | 26.8 | 20.0 | 2.02 |
| Palm (16:0)-oleoyl (18:1) | Palm (16:0)-oleoyl (18:1) | 100 | 12.4 | 27.2 | 22.3 | 1.80 |
|  |  | 300 | 10.5 | 24.4 | 19.7 | 1.88 |
| Dioleoyl (18:1) | Palm (16:0)-oleoyl (18:1) | 100 | 12.9 | 30.8 | 24.0 | 1.86 |
|  |  | 300 | 10.6 | 29.5 | 21.8 | 2.06 |
| Palm (16:0)-oleoyl (18:1) | Myr (14:0)-oleoyl (18:1) | 100 | 13.4 | 29.3 | 23.1 | 1.72 |
|  |  | 300 | 9.9 | 27.0 | 20.6 | 2.08 |
| Dioleoyl (18:1) | Dioleoyl (18:1) | 100 | 11.2 | 26.1 | 20.8 | 1.86 |
|  |  | 300 | 11.9 | 26.7 | 21.1 | 1.77 |
| Bovine | Egg | 100 | 12.8 | 27.6 | 23.4 | 1.83 |
|  |  | 300 | 10.5 | 22.9 | 19.4 | 1.85 |

EXAMPLE 4

PT Reagents made using Full Length recombinant Human Tissue Factor and Synthetic Phospholipids—Effect of Varying the Nature of the Fatty Acid Side Chain Moiety of the Phospholipid—Lyophilized Reagent Purified recombinant human tissue factor, at 300 ng/mL, was combined with mixtures of synthetic phosphatidyl serine (PS) and synthetic phosphatidyl choline (PC) in a PS:PC ratio of 30:70 and a ratio of rTF:phospholipid of 1:10,000. The formulation also included 30 mM TAPSO, 11 mM $CaCl_2$, 215 mM NaCl, 3% glycine, pH 7.4. The mixtures were dispensed into vials and freeze-dried. Results are given as clotting times and were determined using an MLA Electra 800 photo-optical coagulation timer. The test plasmas are a normal lyophilized control, Ci-Trol 1 (COL 1), an abnormal lyophilized control, Ci-Trol II (COL 2), a pool of fresh normal plasmas (FNP) and a lyophilized pool of plasmas from patients receiving warfarin (WARFARIN). The column under RAT is the ratio of the of the PT value of the warfarinized plasma pool divided by the PT value of the normal plasma pool. This ratio is a measure of sensitivity of the reagents. Two controls were included in the testing. The 10F control, lipidated with the natural phospholipids bovine PS and egg PC, was the 10F formulation given in Example II. The other control, Thromboplastin IS, is a commercially available high sensitivity rabbit brain-based thromboplastin reagent, Thromboplastin IS. See Data Table 4.

DATA TABLE 4

| PS Description | PC Description | Col 1 | Col 2 | FNP | Warf | Rat |
|---|---|---|---|---|---|---|
| Dioleoyl (18:1) | Dipalmitoleoyl (16:1) | 13.0 | 33.2 | 11.6 | 30.1 | 2.59 |
| Palm (16:0)-oleoyl (18:1) | Dipalmitoleoyl | 13.4 | 33.7 | 11.9 | 30.1 | 2.53 |
| Dimyristoyl (14:0) | Dioleoyl (18:1) | 19.4 | 54.2 | 16.9 | 53.0 | 3.14 |
| Dioleoyl (18:1) | Dipalmitoyl (16:0) | 17.1 | 43.7 | 15.6 | 37.7 | 2.42 |
| Palm (16:0)-oleoyl (18:1) | Dioleyol (18:1) | 12.6 | 33.2 | 11.5 | 29.5 | 2.57 |
| Palm (16:0)-oleyol (18:1) | Palm (16:0)-oleoyl (18:1) | 12.8 | 33.1 | 11.8 | 30.0 | 2.54 |
| Dioleoyl (18:1) | Palm (16:0)-oleoyl (18:1) | 13.0 | 35.2 | 11.8 | 31.2 | 2.64 |
| Palm (16:0) | Myris (14:0) | 11.8 | 28.6 | 11.3 | 24.2 | 2.14 |

DATA TABLE 4-continued

| PS Description | PC Description | Col 1 | Col 2 | FNP | Warf | Rat |
|---|---|---|---|---|---|---|
| -oleoyl (18:1) | -oleoyl (18:1) | | | | | |
| Dioleyol (18:1) | Dioleoyl (18:1) | 12.3 | 33.6 | 11.0 | 31.0 | 2.82 |
| Bovine Brain | Egg | 13.5 | 35.9 | 12.1 | 34.2 | 2.83 |
| 10F | | 13.3 | 38.2 | 11.7 | 35.4 | 3.03 |
| THROMBOPLASTIN-IS | | 14.2 | 37.6 | 13.5 | 27.4 | 2.03 |

EXAMPLE 5

PT reagents made using Truncated recombinant Human Tissue Factor and Synthetic Phospholipids—Effect of Varying the Nature of the Fatty Acid Side Chain Moiety of the Phospholipid—Lyophilized Reagents Purified recombinant human tissue factor, containing 243 residues and missing most of the cytoplasmic portion of the molecule, was combined with mixtures of synthetic phosphatidyl serine (PS) and synthetic phosphatidyl choline (PC) in a PS:PC ratio of 30:70 and a ratio of rTF:phospholipid of 1:10,000. The formulation included 300 ng/mL rTF, 30 mM TAPSO, 11 mM $CaCl_2$, 215M NaCl, 3% glycine, pH 7.4. Mixtures were dispensed into vials and freeze-dried. Results are given as clotting times and were determined using an MLA Electra 800 photo-optical coagulation timer. The test plasmas are a normal lyophilized control, Ci-Trol 1 (COL 1), an abnormal lyophilized control, Ci-Trol II (COL 2), a pool of fresh normal plasmas (FNP) and a lyophilized pool of plasmas from patients receiving warfarin (WARFARIN). The column under RATIO is the ratio of the of the PT value of the warfarinized plasma pool divided by the PT value of the normal plasma pool. This ratio is a measure of sensitivity of the reagents. Three controls were included in the testing, one was full length rTF as in previous examples, a second was truncated rTF lipidated with natural phospholipids, bovine PS and egg PC, and the third is a commercially available high sensitivity rabbit brain-based thromboplastin reagent, Thromboplastin IS. See Data Table 5.

EXAMPLE 6

PT Reagents made using Truncated recombinant Human Tissue Factor and Synthetic Phospholipids—Effect of Varying the Concentration of rTF and the Reagent Composition Purified recombinant human tissue factor, containing 243 residues and missing most of the cytoplasmic portion of the molecule, was combined with 30:70 mixtures of synthetic phospholipids at a rTF:phospholipid ratio of 1:10,000. Formulation A included synthetic 1-palmitoyl-2-oleoyl phosphatidyl serine (POPS) and dioleoyl phosphatidyl choline (DOPC), 60 mM HEPES, 11 mM $CaCl_2$, 200 mM NaCl, 4.6% glycine, 5 mg/L polybrene, pH 7.4. Formulation B included in the same POPS and DOPC concentrations, 60 mM HEPES, 11 mM $CaCl_2$, 215 mM NaCl, 4.6% glycine, 5 mg/L polybrene, pH 7.4. Formulation C included dioleoyl phosphatidyl serine (DOPS) and DOPC, 40 mM TAPSO, 11 mM $CaCl_2$, 220 mM NaCl, 2.1% glycine, pH 7.4, mixtures were dispensed in vials and freeze-dried. Results are given as clotting times and were determined using an MLA Electra 800 photo-optical coagulation timer. The test plasmas are a normal lyophilized control, Ci-Trol 1 (COL 1), an abnormal lyophilized control, Ci-Trol II (COL 2), a pool of fresh normal plasmas (FNP) and a lyophilized pool of plasmas from patients receiving warfarin (WARFARIN). The column under RATIO is the ratio of the of the PT value of the warfarinized plasma pool divided by the PT value of the normal plasma pool. This ratio is a measure of sensitivity of the reagents. A commercially available high sensitivity rabbit brain-based thromboplastin reagent, Thromboplastin IS, is included as a control. See Data Table 6.

DATA TABLE 5

| PS Description | PC Description | Col 1 | Col 2 | FNP | Warf | Rat |
|---|---|---|---|---|---|---|
| TRUNCATED (243aa) rTF | | | | | | |
| Bovine Brain | Egg | 12.0 | 34.4 | 11.3 | 33.6 | 2.97 |
| Dioleoyl (18:1) | Diolcoyl (18:1) | 11.7 | 34.2 | 11.0 | 37.1 | 3.37 |
| Palm (16:0) -oleoyl (18:1) | Dioleoyl (18:1) | 12.1 | 33.9 | 11.6 | 36.1 | 3.11 |
| Palm (16:0) -oleoyl (18:1) | Palm (16:0) -oleoyl (18:1) | 12.3 | 34.0 | 11.9 | 34.7 | 2.92 |
| Dioleoyl (18:1) | Palm (16:0) -oleoyl (18:1) | 11.6 | 31.0 | 11.1 | 31.9 | 2.87 |
| Palm (16:0) -oleoyl (18:1) | Myris (14:0) -oleoyl (18:1) | 12.7 | 36.6 | 12.4 | 36.3 | 2.93 |
| FULL LENGTH rTF | | | | | | |
| Bovine Brain | Egg | 12.6 | 33.4 | 12.5 | 34.4 | 2.75 |
| Thromboplastin-IS | | 13.2 | 32.5 | 13.5 | 26.9 | 1.99 |

Data TABLE 6

| FORMULATION | rTF Conc.(ng/mL) | COL 1 | COL 2 | FNP | WARFARIN | RATIO |
|---|---|---|---|---|---|---|
| A | 100 | 14.2 | 32.1 | 14.8 | 35.2 | 2.38 |
|   | 150 | 13.3 | 31.5 | 13.9 | 33.2 | 2.41 |
|   | 180 | 12.9 | 31.4 | 13.6 | 33.0 | 2.43 |
|   | 200 | 12.7 | 33.2 | 13.3 | 32.9 | 2.47 |
|   | 240 | 12.7 | 32.3 | 13.3 | 32.9 | 2.47 |
|   | 260 | 12.4 | 33.5 | 13.1 | 33.1 | 2.53 |
| A | 220 | 11.9 | 29.0 | 12.5 | 31.0 | 2.48 |
| B | 240 | 13.0 | 33.3 | 13.7 | 34.5 | 2.52 |
| C | 165 | 13.3 | 29.2 | 13.9 | 33.5 | 2.41 |
| THROMBOPLASTIN - IS |   | 14.0 | 35.3 | 2.5.5 | 29.2 | 1.88 |

EXAMPLE 7

PT Reagents made using Truncated recombinant Human Tissue Factor and Synthetic Phospholipids—Effect of Varying the POPS:DOPC Ratio and the Reagent Composition Purified recombinant human tissue factor, containing 243 residues and missing most of the cytoplasmic portion of the molecule, was combined with varyi mixtures of synthetic 1-palmitoyl-2-oleoyl phosphatidyl serine (POPS) and dioleoyl phosphatidyl choline (DOPC) at a ratio of rTF:phospholipid of 1:10,000. Formulation A included 220 ng/mL rTF with different ratios of POPS:DOPC, 60 mM HEPES, 11 mM $CaCl_2$, 215 mM NaCl, 4.6% glycine, 5 mg/L polybrene, pH 7.4. Formulation B included 240 ng/mL rTF with 30:70 POPS:DOPC, 60 mM HEPES, 11 mM $CaCl_2$, 215 mM NaCl, 4.6% glycine, pH 7.4. Formulation C included 165 ng/mL rTF with 30:70 POPS:DOPC, 40 mM TAPSO, 11 mM $CaCl_2$, 220 mM NaCl, 2.1% glycine, pH 7.4. Mixtures were dispensed into vials and freeze dried. Results are given as clotting times and were determined using an MLA Electra 800 photo-optical coagulation timer. The test plasmas are a normal lyophilized control, Ci-Trol I (COL 1), an abnormal lyophilized control, Ci-Trol II (COL 2), a pool of fresh normal plasmas (FNP) and a lyophilized pool of plasmas from patients receiving warfarin (WARFARIN). The column under RATIO is the ratio of the of the PT value of the warfarinized plasma pool divided by the PT value of the normal plasma pool. This ratio is a measure of sensitivity of the reagents. A commercially available high sensitivity rabbit brain-based thromboplastin reagent, Thromboplastin IS, is included as a control. See Data Table 7.

(b) a mixture of synthetic phospholipids in an amount sufficient to activate said protein wherein at least one of the phospholipids has an unsaturated fatty acid side chain;

(c) a buffer composition; and (d) calcium ion in an amount sufficient to activate the recombinant protein.

2. The prothrombin time reagent of claim 1 wherein the unsaturated fatty acid side chains is selected from the group consisting of carbon chain lengths 14, 16 and 18.

3. The prothrombin time reagent of claim 1 wherein the synthetic phospholipids are selected from the group consisting of dioleoyl (18:1)-PS, palmitoyl (16:0)-oleoyl (18:1)-PS, dimyristoyl (14:0)-PS, dipalmitoleoyl (16:1)-PC, dipalmitoyl (16:0)-PC, dioleoyl (18:1)-PC, palmitoyl (16:0)-oleoyl (18:1)-PC, and myristoyl (14:0)-oleoyl (18:1)-PC.

4. A prothrombin time reagent comprising:

(a) a recombinant protein having the amino acid sequence of human tissue factor;

(b) a mixture of synthetic phospholipids in an amount sufficient to activate said protein wherein at least one of the phospholipids has an unsaturated fatty acid side chain;

(c) a buffer composition; and (d) calcium ion in an amount sufficient to activate the recombinant protein.

5. The prothrombin time reagent of claim 4 wherein the unsaturated fatty acid side chains is selected from the group consisting of carbon chain lengths 14, 16 and 18.

6. The prothrombin time reagent of claim 4 wherein the synthetic phospholipids are selected from the group consisting of dioleoyl (18:1)-PS, palmitoyl (16:0)-oleoyl (18:1)-PS, dimyristoyl (14:0)-PS, dipalmitoleoyl (16:1)-PC, dipalmi- Data TABLE 7

| FORMULATION | PS:PC | COL 1 | COL 2 | FNP | WARFARIN | RATIO |
|---|---|---|---|---|---|---|
| A | 25:75 | 12.4 | 31.1 | 13.7 | 33.3 | 2.43 |
|   | 30:70 | 11.5 | 28.2 | 12.5 | 30.4 | 2.43 |
|   | 35:65 | 11.1 | 24.8 | 12.0 | 26.7 | 2.43 |
| A | 30:70 | 11.6 | 27.7 | 12.5 | 30.3 | 2.42 |
| B | 30:70 | 12.6 | 31.4 | 13.4 | 34.4 | 2.57 |
| C | 30:70 | 12.0 | 26.8 | 13.1 | 34.0 | 2.60 |
| THROMBOPLASTIN - IS |   | 14.1 | 35.5 | 15.2 | 29.8 | 1.96 |

We claim:

1. A prothrombin time reagent comprising:

(a) a recombinant protein having an amino acid sequence corresponding to the cytoplasmic portion of human tissue factor;

toyl (16:0)-PC, dioleoyl (18:1)-PC, palmitoyl (16:0)-oleoyl (18:1)-PC, and myristoyl (14:0)-oleoyl (18:1)-PC.

7. A prothrombin time reagent comprising:

(a) a recombinant protein having an amino acid sequence corresponding to the cytoplasmic portion of human tissue factor;

(b) a mixture of synthetic phospholipids in an amount sufficient to activate said protein wherein at least one of the phospholipids has an unsaturated fatty acid side chain;

(c) a buffer composition; and (d) calcium ion in an amount sufficient to activate the recombinant protein, wherein the amino acid sequence of the protein contains the point mutation Cysteine 245 to Serine.

8. A prothrombin time reagent comprising:

(a) a recombinant protein having the amino acid sequence of human tissue factor;

(b) a mixture of synthetic phospholipids in an amount sufficient to activate said protein wherein at least one of the phospholipids has an unsaturated fatty acid side chain;

(c) a buffer composition; and (d) calcium ion in an amount sufficient to activate the recombinant protein, wherein the amino acid sequence of the protein contains the point mutation Cysteine 245 to Serine.

9. A composition useful in a prothrombin time reagent said composition comprising a mixture of synthetic phospholipids wherein the synthetic phospholipids are added to said prothrombin time reagent in an amount necessary to activate said reagent and wherein at least one of the synthetic phospholipids has an unsaturated fatty acid side chain.

10. The composition of claim 9 wherein the unsaturated fatty acid side chains of the synthetic phospholipids are selected from the group consisting of carbon chain lengths 14, 16, and 18.

11. The composition of claim 9 wherein the synthetic phospholipids are selected from the group consisting of dioleoyl (18:1)-PS, palmitoyl (16:0)-oleoyl (18:1)-PS, dimyristoyl (14:0)-PS, dipalmitoleoyl (16:1)-PC, dipalmitoyl (16:0)-PC, dioleoyl (18:1)-PC, palmitoyl (16:0)-oleoyl (18:1)-PC, and myristoyl (14:0)-oleoyl (18:1)-PC.

* * * * *

UNITED STATES PATENT AND TRADEMARK OFFICE
CERTIFICATE OF CORRECTION

PATENT NO. : 5,625,036
DATED : April 29, 1997
INVENTOR(S) : Pamela L. Hawkins, Liliana Tejidor, James Maynard, Kevin Johnson It is certified that error appears in the above-identified patent and that said Letters Patent is hereby corrected as shown below:

In claim 1 at column 13, line 66, "corresponding to" should read --missing most of--. In claim 7 at column 14, line 66, "corresponding to" should read --missing most of--.

Signed and Sealed this

Third Day of March, 1998

*Attest:*

BRUCE LEHMAN

*Attesting Officer*     *Commissioner of Patents and Trademarks*